United States Patent [19]

Welker

[11] Patent Number: 4,463,599
[45] Date of Patent: Aug. 7, 1984

[54] FREE WATER VOLUME ANALYZER

[75] Inventor: Robert H. Welker, Sugar Land, Tex.

[73] Assignee: Welker Engineering Company, Sugar Land, Tex.

[21] Appl. No.: 470,311

[22] Filed: Feb. 28, 1983

[51] Int. Cl.³ .................... G01N 1/10; G01N 33/26; E21B 49/00
[52] U.S. Cl. .................. 73/61.1 R; 73/864.62; 73/864.91
[58] Field of Search ............. 73/61 R, 61.1 R, 864.62, 73/864.91

[56] References Cited

U.S. PATENT DOCUMENTS 2,637,211  5/1953  Norman ........................ 73/864.62
4,172,670 10/1979  Welker ...................... 73/864.62 X

FOREIGN PATENT DOCUMENTS 2042471  9/1980  United Kingdom ............ 73/61.1 R

*Primary Examiner*—James J. Gill
*Attorney, Agent, or Firm*—Gunn, Lee & Jackson

[57] ABSTRACT

In the preferred and illustrated embodiment, a sample collection system is set forth which includes a free water volume analyzer. Sample from a producing well or pipeline is collected in this apparatus. The sample is stored under pressure. As the sample is collected, there is some risk that water will be collected with it. The sample collection apparatus is demounted after the full sample has been collected and moved to a laboratory for analysis. The value of the flow is gauged by the sample or specimen stored in this apparatus. At the time of testing, it is necessary to check for water content, water having no sale value. This apparatus includes a bottom located water collection chamber with a piston plugging that chamber. The piston is forced down in a controlled fashion and the water is viewed through a sight glass. The sight glass enables the test personnel to determine by sight whether or not there is water in the sample.

10 Claims, 3 Drawing Figures

FREE WATER VOLUME ANALYZER

BACKGROUND OF THE DISCLOSURE

This apparatus is a sample collection apparatus intended to be used with an oil field collection system or between a buyer and seller of light hydrocarbons. One typical location is at a custody transfer point where a purchaser gathers oil into a flow line. Typically, this device will be installed downstream from a producing well, or perhaps several wells connected to a gathering line. This apparatus is connected to the transfer line which removes the collected sample after it has been produced. Sample collection and removal is accomplished after collection for a specified interval. For instance, the sample collection apparatus might be operated for one month whereupon it is removed and replaced by a duplicate apparatus which collects sample for the next month. Often, a separator will produce light ends. These lighter molecules vaporize more readily and are often separated to be stripped into butane or propane. Such light ends are often sold separately, for instance, as butane or propane.

An alternate place of installation is on a line between a buyer and seller of lighter hydrocarbons. Briefly, this might arise in the context of selling refined light molecule hydrocarbons delivered through a line between the selling plant and buying plant. The pipeline stream is typically partially refined and sediment has been removed. The heavier molecules have been removed. The flowing liquid is typically almost free of color, tending to be clear, almost as clear as water in small samples. Assume that the sample is as clear as water. Even in this case, the sample-water interface can be seen in the present apparatus on inspection of accumulated sample.

The contract prices involved may place great importance on the assay of the sample. Over a few days while a sample is collected, the sales of flowing hydrocarbons may total in the millions of dollars. For this reason, sample collection must be accurate and the assay of the sample must be accurately done. In many instances, the sample collection apparatus may collect a very large sample in a fixed cylinder. The cylinder is filled to some maximum volume. The sample is mixed thoroughly as described below. The very large sample is then transferred from the very large cylinder to several small cylinders. As an example, the thoroughly mixed sample is split and transferred into three smaller cylinders which might be denoted as transport cylinders. One is for the buyer, another is for the seller, and a third is for a referee or archieve purposes. As an example, the large cylinder may collect many, perhaps as many as 50 liters while the three transport cylinders each receive and store 10 liters. This invention can be scaled up or down to provide all of the sample receiving cylinders.

The sample collection apparatus of this disclosure is intended for use with sample furnished under pressure. Not only is the sample received under pressure, it is stored under pressure. There is risk that the sample may boil off if it is stored at reduced pressure. Consider as an example collection of the sample at 900 psi. If the gathering line is operated at 900 psi, the sample should also be stored at 900 psi. If it is stored only at atmospheric pressure, there is great risk that lighter hydrocarbons will boil off and the heat content of the sample will be changed as a result of this loss. This loss not only deviates the data, but it also makes storage far more difficult, it being much easier to contain a specified volume within a sealed container as a liquid at elevated pressure. In view of these requirements, back pressure is loaded in the storage container to assure that the pressure of the stored product is maintained in the desired range. This back pressure must be overcome to achieve sample storage. The sample volume is expanded to receive more sample until the storage device is adequately filled.

The sample collection apparatus, having been filled, is then removed and carried away to a test laboratory or other facility. It is optimum that the test be conducted on the container at the same elevated pressure. The device is therefore disconnected from the typical field installation and moved by means of a truck or the like to a laboratory facility. At the laboratory facility, the sample storage container is then connected to deliver the sample to test equipment typically including a chromatograph to determine complete hydrocarbon analysis. Typically, the contract price paid for oil is adjusted according to the hydrocarbon analysis of the sample. In the laboratory, one of the tests applied to the sample is to determine the actual volume of B S & W. This refers to basic sediment and water. This is the trash which is collected in the sample. There is a limit on the B S & W. The limit is typically stated as a percentage. This limit is applied to the sample. A typical size for the sample collection apparatus of this disclosure is 500 cubic centimeters volume. A volumetric sample of this size is deemed to be quite representative of a flow subjected to sampling and analysis in accordance with the teachings of this disclosure. Of course, some samples may be as large as 20,000 cc.

The B S & W specification may limit the total content to 3% or less. Above this level, the sample will be rejected. Below this level, the sample will be accepted. The seller may be required to filter and dewater to reduce B S & W to an acceptable level; often, the produced oil is stored in a tank so that cleaning of the oil to reduce B S & W is not easily done. It is expensive and time consuming to clean the oil to reduce B S & W.

The B S & W normally settles to the bottom. This apparatus includes a bottom located sight glass. The sight glass is sized to hold more than the specified maximum quantity of B S & W. Assume for purposes of illustration that the maximum permissible quantity of B S & W is 2%. On a volume of 500 cc, this amounts to 10 cc. A volume of 10 cc of B S & W is the maximum; this apparatus includes a sight glass volume which exceeds 2% so the interface between the B S & W at the bottom and the petroleum thereabove can be observed. The sight glass and its associated chambers are sized so that perhaps 5% of the total volume is located in this chamber. In other words, the B S & W up to the permissible maximum is visable within the sight glass to see the oil-water interface. In lighter molecules, the accumulated sample is usually rather clear, often as clear as water. In some instances, the two liquids separate at an interface which is difficult to see. This device locates that interface at an easily seen location.

This system thereby accomodates B S & W up to the specified permissible maximum. It enables the laboratory personnel to check for B S & W content. The goal of the laboratory test is to determine pricing dependent on the sample. Most laboratories test the sample on a chromatograph. The routine procedure of testing does not determine water content in the sample. Thus, even before the sample is analyzed by peak detection in a chromatograph, the water content can be determined by the present apparatus. The water-hydrocarbon interface is located in the sight glass. This location is converted into a percentage of total sample. Sample data can be corrected with this information.

With the foregoing in view, the present apparatus is summarized as a sample collection apparatus. It accumulates sample to a specified volume against a specified back pressure. Moreover, it includes a bottom located B S & W collection chamber sized to receive a certain portion of B S & W to enable quick observation, enabling laboratory personnel to observe and measure the total B S & W. Further, the B S & W sample collection apparatus includes a bottom located sight gauge. The sight gauge is normally closed with a product piston filling the sight area. The piston can be lowered after the main cylinder has received a sample sufficiently sized to fill the sight glass area. The main piston keeps pressure on the sample to prevent flashing, namely, boil off of the lighter hydrocarbon molecules.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
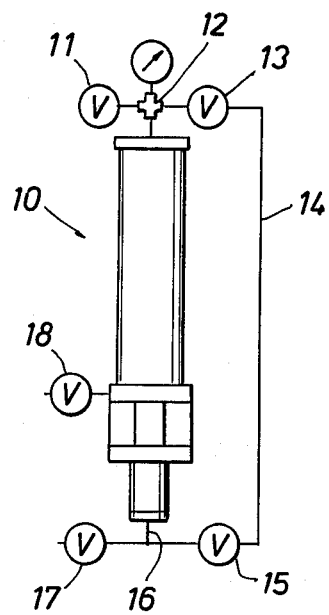
FIG. 1 is a schematic of connections for use with the sample collection apparatus of this disclosure showing the sample collection apparatus and the externally located lines controlling its operation.

Attention is directed first to FIG. 1 of the drawings. There, the sample collection apparatus including a free water volume analyzer is illustrated in outline form and is identified by the numeral 10. It incorporates a valve 11 which is connected to a suitable charging source such as compressed nitrogen. It connects with a regulator 12. In turn, the regulator 12 is connected with a valve 13. The valve 13 supplies a line 14 which connected to a valve 15. The valve 15 connects through a tee 16 and then to a vent valve 17. Product is introduced through a valve 18. Ordinarily, the product is supplied through the valve 18 which is turned on at the time installation of the sample collection apparatus 10. The valve 11 is used at the preliminary gas charging stage, there being a source of pressurized nitrogen or some other inert gas which is used to charge the sample collection apparatus 10. Charge is accumulated to a specified maximum pressure. Initially, there is no sample in the sample collection apparatus; eventually, it is filled to some specified maximum. It is filled against back pressure which is regulated by the regulator 12. Operation of the several valves will be set forth in describing the operation of the device.

Figure 2:
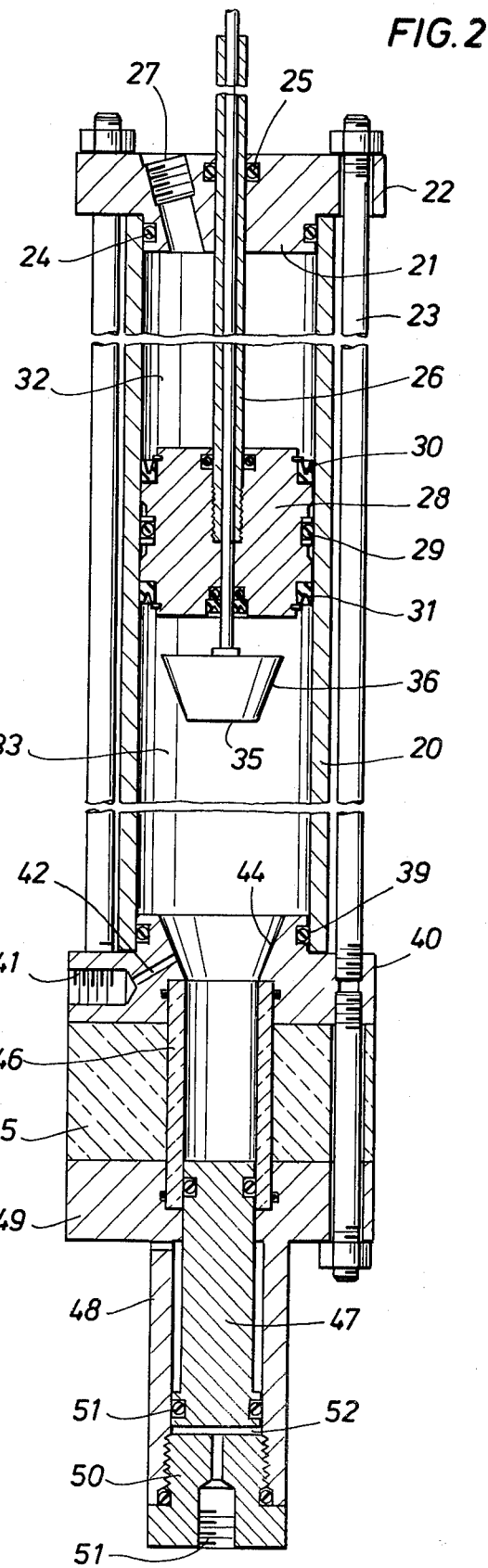
FIG. 2 shows the sample collection apparatus in full length with a sectional cut to expose internal details of construction.

FIG. 2 of the device discloses in sectional view an elongate cylindrical housing 20. It supports a head 21 at the top end. The head 21 is secured to the cylindrical housing 20 by means of a protruding lip 22 which is drilled to receive multiple threaded tie rods 23. The tie rods 23 encircle the head 21. As the apparatus is assembled, leaks between the components just mentioned are prevented by means of seals 24 on the exterior and 25 on the interior. The seal 25 is immediately adjacent to a centrally located elongate hollow indicator rod 26. The rod 26 passes through the head 21 at a central drilled hole. It stands above the head 21. It moves upwardly to indicate filling of the cylindrical housing 20. The head 21 is also drilled with a tapped opening 27, and this is incorporated to connect to the regulator 12 and the valves 11 and 13.

The indicator rod 26 is a talisman indicating the volume stored in the apparatus. If for instance, the cylindrical housing has a length of 20 centimeters, the rod can be marked by means of calibration marks, color coding or the like to indicate that it has risen to 20 centimeters, thereby indicating the amount of stored specimen in the cylindrical housing 20. There is an interface piston 28 connected to the indicator rod. It is threaded to the rod 26, the two moving as a unit. The interface piston seals against the inside wall of the cylindrical housing 20. To this end, the piston supports a centrally located seal ring 29 and similar seals 30 and 31 at the upper and lower ends of the interface piston. The piston 28 is thus sealed against leakage. It completely plugs the cylindrical housing 20 and divides it into an upper chamber and a lower chamber. The upper chamber is identified by the numeral 32 while the lower chamber is identified at 33.

The indicator rod is drilled axially and is hollow. It threads on its exterior to the interface piston 28. The rod 26 is sufficiently long that it clears the top end of the cylinder head 21. The rod 26 encloses a mixture push rod on the interior. The push rod telescopes within the indicator rod. Moreover, the rod extends fully to support a mixing plate 35 at the lower end. The mixing plate 35 is located in the bottom chamber 33. It will be observed that the plate 35 can be reciprocated by hand motion applied to the push rod. It is reciprocated to stir or mix the sample which is stored in the chamber 33 as will be described. The mixing plate is tapered on the exterior and includes a tapered external face 36 to nest with the other equipment as will be described.

Continuing with the description of FIG. 2, there is a lower cylinder head. The cylinder head abutts against the housing 20 and clamps to it. A seal 39 prevents leakage around the housing. The lower cylindric head has a surrounding peripheral shoulder 40 drilled with holes at spaced locations to match those at the encircling flange 22 at the upper end, and the tie rods 23 extend into the lower head and align relative to additional head studs. The lower cylinder head is drilled at 41 with an inlet passage enabling threaded connection to be made with the product inlet valve 18. The tapped opening connects with a passage 42 which admits sample through the valve 18 into the lower storage chamber 33. The cylinder head has a tapered seat area 44. This seat is tapered to contact against and seat with the outer shoulder 36 of the mixing plate 35. Sample is introduced into the chamber 33 and is stored in that chamber beneath the interface piston 28.

The lower head is concentric with and adjacent to a transparent spacer. This is identified at 45, and has the form of a solid acrylic body. It is transparent so the interior can be viewed. The acrylic surrounds a tempered glass sleeve 46. They are both concentrically arranged around a sight gauge piston 47. The sight gauge piston 47 has two positions, one being retracted as shown in FIG. 2 and the other being the up or extended position of FIG. 3. The movement will be described below.

Figure 3:
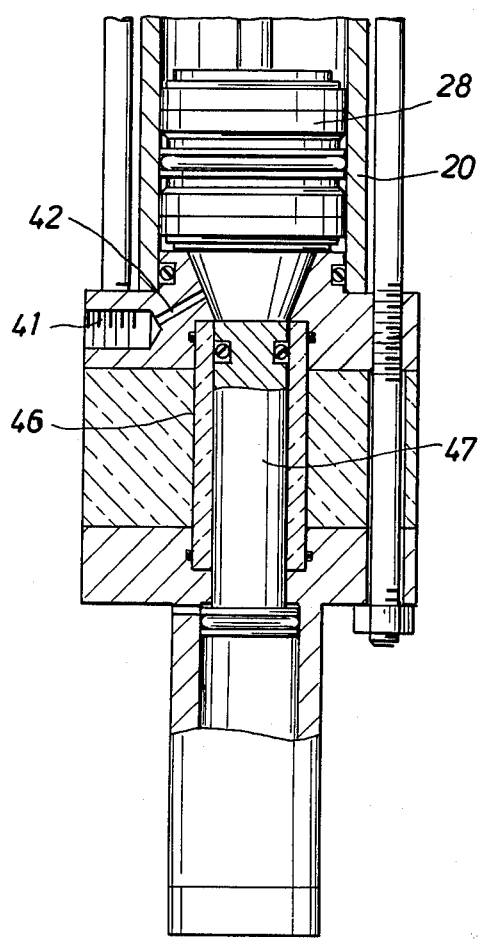
FIG. 3 is a partial view similar to FIG. 2 showing the initial position of the product piston relative to the sight gauge.

The piston 47 is received within a cylindrical housing 48 which terminates at a circular flange 49. The flange 49 aligns with the flange 40 on the facing lower cylinder head, and the studs fasten through the flange 49 thereby enabling clamping to assemble the apparatus. The lower cylindrical extension 48 is affixed to the surrounding flange 49 and is axially hollow. The extension is sealed at the end by means of a threaded plug 50, the plug being drilled with a tapped opening 51. The opening 51 is adapted to connect to the tee 16 shown in FIG. 1. The gauge piston 47 includes a bottom located surrounding lip supporting a seal 51. There is a chamber 52 below the gauge piston 47. Fluid under pressure introduced into the chamber 52 through the tapped opening 51 forces the piston 47 upwardly. The initial condition is shown in FIG. 3, and there it will be observed that the sight gauge piston 47 has risen to the point where it is flush with the top end of the glass sleeve 46. Suitable seal rings prevent leakage along the clear glass sleeve 46.

Operation of the device will assist in an understanding of this equipment. One sequence of operation involves the following. The initial condition finds the interface piston 28 at the extremity of its travel. This is shown in FIG. 3. It forces the mixing plate 35 against the tapered face 44 for receiving the tapered mixing plate. The lower chamber 33 is reduced to a de minimus volume. The upper chamber 32 is at maximum size. Through the use of the valve 11 and the regulator 12, the upper chamber 32 is filled with a preliminary charge. The pressure is limited by the strength of the structure, and a typical maximum is in the range of 1800 psi. Pressure is charged to some specified level, perhaps 800 psi. This representative pressure level is sustained by operation of the regulator. The valve 13 is opened so that the charging gas flows through the line 14 and the valve 15. This supplies the same charging pressure through the tee 16. No venting occurs because the valve 17 is closed. This piston 47 is held up.

Assume that sample is collected and forced into the chamber 33. It flows through the valve 18. It fills the lower chamber 33. It initially forces the interface piston up, and the tapered mixing plug 35 is lifted also. The sample collects above the sight gauge piston 47 which is in the up or raised position of FIG. 3. If the initial charge placed in the topmost chamber is 800 psi, then the sample that is introduced must be received at a pressure of 800 psi to force the piston upwardly. In other words, the sample pressure must exceed 800 psi in this example. Needless to say, it could be regulated at some different pressure depending on requirements.

As sample is accumulated, the interface piston 28 is forced upwardly. The mixing plate 35 is forced against it. They move upwardly as a unit. As they move, the volume in the lower chamber 33 expands to receive more sample. The volume in the upper chamber is reduced. As it is reduced, preliminary charged gas is forced out through the regulator 12. It is vented to atmosphere. This continues until the interface piston is forced to the end of its travel. At the top end of travel, the indicator rod is at its maximum extension. The pressure of the sample remains at 800 psi preset for this example. Then, service personnel can remove the apparatus from the field and carry it to the laboratory for inspection. Of course, alternate regulated pressures can be used; no regulator can be used; various systems can be selected.

At this juncture, the product line is disconnected from the inlet valve 18. This is accomplished by first closing the inlet valve 18. The device is then carried to a laboratory for testing. At the laboratory, the inlet valve 18 is connected to test equipment. Testing can be carried out at this time. The valve 11 is also connected to a source of high pressure gas, typically nitrogen. Before testing occurs, it is desirable to view the sample which has been collected in the apparatus. The sample container 10 is held stationary for a few minutes to permit the sediment to collect at the bottom and the water-petroleum interface to be established. This is initiated by holding the apparatus stationary without agitation. Further, the valve 15 is momentarily closed. The valve 17 is opened to vent. As this occurs, the sight gauge piston 47 retracts or moves downwardly to the position shown in FIG. 2. When it moves down, it exposes the chamber that is visible within the sight glass 46. The specimen can then be viewed to determine if the B S & W is excessive.

Consider as an example the following scale values. Assume that the interface piston 28, moved to the top extremity of movement, leaves a chamber therebelow which holds 500 cc sample. The volume exposed to view should be perhaps 3%, assuming that the B S & W is to be a lesser percentage. If B S & W is to be only 2% or less, then the volume is perhaps slightly more than 2%. In one embodiment, where the sample storage apparatus collects a sample of 500 cc volume, the volume that is visible within the sight glass is about 12.3 cc. The water-petroleum interface is easily seen in the sight glass after settling has occurred. When the piston 47 is lowered, the B S & W settles into the visible area and can be observed. Even should there be no particulate sediment and all the liquids are clear, there is an oil-water interface which can be viewed after settling of the B S & W. It can be viewed from the side by looking through the transparent components into the chamber just above the sight gauge piston 47.

Generally, it is undesirable to view the B S & W repetitively. Typically, one view is adequate and that preferably occurs after the sample storage apparatus has been demounted in the field and removed to the laboratory for delivery of the sample. After the sample has been delivered, the valve 18 is fully opened to deplete all sample from the chamber 33. If desired, the chamber 33 can be washed with some suitable solvent. Thereafter, the device can be prepared for return to the field. This might require two or three washings with solvent to clear the chamber 33. After washing, the preliminary gas charge is placed in the chamber 32 by operation of the valves 11, 13 and 15, and the device is then carried to a remote location.

Delivery of the sample may require some stirring or agitation. There is a tendency for sample stratification. Stratification is not helpful at the time of running the sample through analytical instruments. This can be overcome by agitating the push rod. This stirs or churns the sample in the chamber 33 by reciprocating the mixing plate 35, the contents are churned and the mixed sample is then delivered.

An advantage of the present apparatus is that it assists test apparatus which receives the sample at the desired elevated pressure. In fact, the B S & W can be observed visually through this apparatus prior to sample delivery. The B S & W is gauged with a goal of determining if the sample is out of the acceptable range for B S & W. Moreover, the sample is delivered after visual inspection without running the risk of vaporizing the light hydrocarbons from the sample.

While the foregoing is directed to the preferred embodiment, the scope is determined by the claims which follow.

What is claimed is:

1. Sample collection apparatus comprising:
   (a) an elongate cylindrical housing;
   (b) a head closing said housing at an upper end;
   (c) piston means within said housing below said head and sealing within said housing for movement therein, said piston means dividing said housing into an upper chamber and a lower chamber;
   (d) a lower head attached to said housing to define a lower chamber below said piston means wherein said lower chamber is adapted to receive and store a sample of interest, and further wherein said upper chamber receives a back pressure charge acting on said piston means to maintain a specified pressure on said piston means;
   (e) sight glass means connected with said lower head and having a chamber communicating with said lower chamber for receiving B S & W into said sight glass means, said sight glass means further including a specified volume for receiving B S & W; and
   (f) sight glass piston means movable in said sight glass means to selectively enable filling of said sight glass means.

2. The apparatus of claim 1 wherein said sight glass piston means plugs a surrounding sight glass of transparent material and said sight glass is aligned with said lower chamber to receive and collect B S & W therein on retraction of said sight glass piston means, and said sight glass comprises said sight glass means.

3. The apparatus of claim 2 further including a pair of spaced flange members securing a sight glass comprising said sight glass means, and further including seal means therearound for sealing against leakage around said sight glass.

4. The apparatus of claim 3 further including a surrounding solid transparent body between said flange member and surrounding said sight glass means.

5. The apparatus of claim 4 wherein said lower chamber receives a mixing plate therein mounted on a mixer rod extending to the exterior of said housing and having a handle enabling said handle to be reciprocated for stirring with said mixing plate.

6. The apparatus of claim 5 further including an elongate hollow indicator rod extending from said piston means and extending upwardly through said upper chamber, and wherein said mixing plate is aligned with said sight glass means.

7. The apparatus of claim 6 wherein said sight glass piston means is received in a cylindrical housing having a piston chamber adjacent to said sight glass piston means for forcing said sight glass piston means into an extended position, and said piston chamber is sealed by seal means, and further including means connecting fluid under pressure from said upper chamber to move sight glass piston means.

8. The apparatus of claim 1 including:
   (a) a gas charging valve means connected to said upper chamber for charging with a gas;
   (b) a gas delivery valve means connected from said upper chamber to a chamber for moving said sight gauge piston means; and
   (c) a valve means for reducing pressure in said chamber for moving said sight gauge piston means.

9. The apparatus of claim 1 including
   (a) inlet valve means connected into said lower chamber;
   (b) a gas flow line connected from said upper chamber; and
   (c) valve means in said gas flow line connected to control gas flow therethrough.

10. The apparatus of claim 1 wherein
    (a) said sight glass piston means plugs said sight glass means;
    (b) a cylindrical housing for said sight glass piston means for selectively receiving said piston means therein; and
    (c) means for introducing fluid under pressure into said housing to move said sight glass piston means.

* * * * *